United States Patent [19]

Hoshi

[11] 4,078,569
[45] Mar. 14, 1978

[54] HAIR TWEEZER DEVICE

[75] Inventor: Sadao Hoshi, Tokyo, Japan

[73] Assignee: Chisho Corporation, Tokyo, Japan

[21] Appl. No.: 686,089

[22] Filed: May 13, 1976

Related U.S. Application Data

[62] Division of Ser. No. 614,743, Sep. 18, 1975, Pat. No. 4,033,350.

[30] Foreign Application Priority Data

Jun. 10, 1975 Japan .................................. 50-69060

[51] Int. Cl.² ............................................... A61N 3/04
[52] U.S. Cl. ................................................. 128/303.13
[58] Field of Search .............. 81/43; 128/303.1, 303.13

[56] References Cited

U.S. PATENT DOCUMENTS

| 1,071,978 | 9/1913 | White | 128/354 X |
| 2,279,068 | 4/1942 | Siebrandt | 81/43 UX |
| 2,417,530 | 3/1947 | Weiser | 128/303.13 |
| 2,888,927 | 6/1959 | Fozard | 128/303.13 |
| 3,999,552 | 12/1976 | Huggins | 128/303.13 |

Primary Examiner—Channing L. Pace

Attorney, Agent, or Firm—Hubbell, Cohen, Stiefel & Gross

[57] ABSTRACT

A device for plucking out hairs by utilizing heat generated by the application of high frequency waves but which prevents the transfer of the heat to the skin. The device comprises a main body substantially in the form of a letter U including a pair of elongated legs and a curved portion which has a certain degree of flexibility. One of such elongated legs is connected to a high frequency wave generator. A pair of hair clamping members formed as hair clamping tongs is connected to the other elongated leg. A link mechanism is arranged in the two legs and coupled to a set lever for moving the tips of the hair clamping members from a position in which they are in engagement with each other, to a position in which they are out of engagement with each other by utilizing the flexibility of the curved portion of the main body so that the hair clamping members can nip, transmit heat to and pluck out a hair in one operation. The means for preventing the transmission of the heat to the skin may be either in the form of a heat insulating cover provided to each of the hair clamping members or a safety guide adapted to keep the tips of the hair clamping members out of direct contact with the skin.

1 Claim, 15 Drawing Figures

HAIR TWEEZER DEVICE

This is a division of application Ser. No. 614,743, filed 9/18/75 now U.S. Pat. No. 4,033,350.

BACKGROUND OF THE INVENTION

This invention relates to a hair tweezer device utilizing heat generated by the application of high frequency waves and provided with means for avoiding direct contact with the skin by the hair clamping members for nipping hairs while in use.

Hair tweezer devices of the aforementioned type which utilize heat generated by a high frequency wave generator have not hitherto been provided with means for avoiding direct contact with the skin by a pair of hair clamping members in spite of the fact that the hair clamping members are heated to an elevated temperature which causes the user to feel hot if they are brought into direct contact with the skin. Thus, when a conventional hair tweezer device of the type utilizing high frequency waves is used, caution must be exercised by the user to avoid direct contact with the skin by the tips of the hair clamping members and adjustments must be effected to the device during the operation of the device.

SUMMARY OF THE INVENTION

This invention has as its object the provision of improvements in or relating to a hair tweezer device for plucking out hairs by utilizing heat generated by the application of high frequency waves, such hair tweezer device comprising means for avoiding direct contact by the tips of the hair clamping members with the skin, so that the safety of the skin of the user can be assured.

The aforementioned object is accomplished in accordance with the present invention by providing a safety guide which can be movable relative to the pair of hair clamping members or by providing a heat insulating cover to each of the hair clamping members whereby the skin can be kept from being brought into direct contact with the heated hair clamping members.

Additional objects and advantages of the invention will become apparent after the description hereinafter set forth is considered in conjunction with the drawings.

Figure 1:
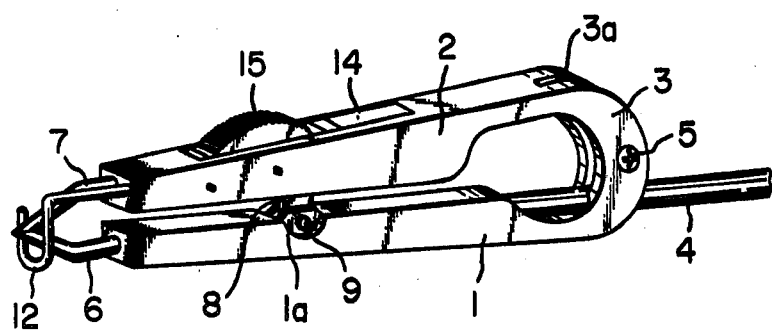
FIG. 1 is a perspective view of the hair tweezer device comprising one embodiment of the invention.
Figure 1A:
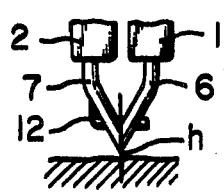
FIG. 1a is a view of the front end portion of the hair tweezer device of FIG. 1 before clamping a hair.
Figure 1B:
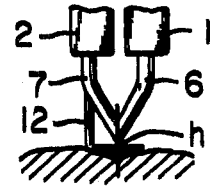
FIG. 1b is a view of the front end portion of the hair tweezer device of FIG. 1 after a hair is clamped.

DESCRIPTION OF THE PREFERRED EMBODIMENTS:

Preferred embodiments of the invention shown schematically in the drawings will now be described in some detail.

Figure 2:
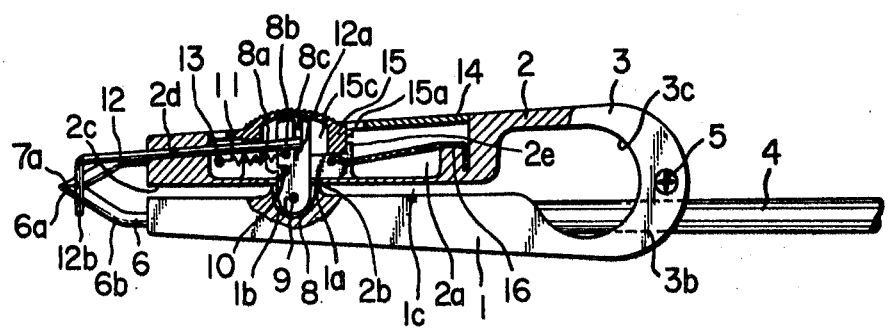
FIG. 2 is a front view, partly shown in section, of the hair tweezer device shown in FIG. 1.

In FIG. 2, the hair tweezer device comprises a main body substantially in the form of a letter U which can be made of metal plastics, particularly light metal. The main body comprises a curved portion 3, and elongated legs 2 and 3 extending from the curved portion 3 and shown in a juxtaposed relationship, the curved portion 3 being slightly flexible. A slit 3a disposed axially in the main body is formed in the curved portion 3 (See. FIG. 1), while a hole 3b is bored at one end of the curved portion 3 to extend longitudinally of one leg 1. A high frequency wave conductor 4 which may be a sealed wire is inserted in the hole 3b and extends in the leg 1 to be connected to the hair clamping members 6 and 7 in the legs. After the high frequency wave conductor 4 is inserted in the hole 3b, a screw 5 may be threadably inserted in holes formed in the curved portion 3, so that the width of the slit 3a can be reduced when the screw 5 is tightened (See FIG. 1).

The hair clamping member 6 extends outwardly from a forward end of the leg 1, is bent at 6b and terminates at a tip 6a. Likewise, the other hair clamping member 7, which forms a pair with the hair clamping member 6, extends outwardly from a forward end of the leg 2, is bent at 7b and terminates at a tip 7a. The leg 1 is provided on its inner surface with a support portion 1a which is disposed nearer to the forward end of the leg 1 than its central portion. The straight inner surface area of leg 1 other than the support portion 1a is a straight inner surface portion 1c which is contiguous with an inner curved surface 3c of the curved portion 3 and spaced apart a predetermined distance from an inner straight surface portion 2c of the leg 2.

Formed in the support portion 1a is a slit 1b which receives therein a setting link 8 which has secured to one end a pin 9 rotatably supported by the support portion 1a. Thus the setting link 8 can be moved in pivotal motion relative to the support portion 1a. The setting link 8 extends upwardly through an aperture 2b formed in the bottom of a hollow space 2a in the leg 2.

The setting link 8 is formed therein with a notch 8a for receiving a locking pin 10, with a hole 8b for connecting one end of a spring 11, and with a slit 8c disposed longitudinally from the setting link 8 for an end portion 12a of a safety guide 12 to be engaged therein. The locking pin 10 is arranged in the hollow space 2a of the leg 2 and extends between two side walls of the leg 2 so that both ends of the pin 10 are supported by the side walls of the leg 2. The spring 11 is connected at the other end thereof to a pin 13 arranged in the hollow space 2a and supported at opposite ends thereof by the side walls of the leg 2. The safety guide 12 engaged at its end portion 12a in the slit 8c extends longitudinally from the leg 2 and emerges at its forward end portion from the leg 2 through a hole 2d bored at a forward end portion of the leg 2. After emerging from the leg 2, the forward end portion of the safety guide 12 is bent in a direction normal to the longitudinal axis of the legs 1 and 2 and then formed into a U-shaped forward end portion 12b.

The hollow space 2a is provided at its top with a cover 14 formed therein with an opening 14a which receives therein a setting lever 15 including a surface 15a which performs the function of guiding the setting lever 15 when the latter moves in sliding movement along the cover 14. A plate spring 16 arranged in the space 2a and secured at one end of an end wall of the leg 2 is pressed upwardly at the other end by the underside of the setting lever 15 for frictionally guiding the setting lever 15 and the cover 14.

The setting lever 15 is formed on its outer periphery with a knurled surface 15b and surrounds the setting link 8 at its inner periphery which is formed therein with an inner peripheral surface adapted to press against the setting link 8 when the setting lever 15 is moved. The setting lever 15 includes side walls which are surrounded by a guide portion 2e of the leg 2 which is in the form of a channel including side walls adapted to guide the side walls of the setting lever 15 in sliding movement.

Figure 3:
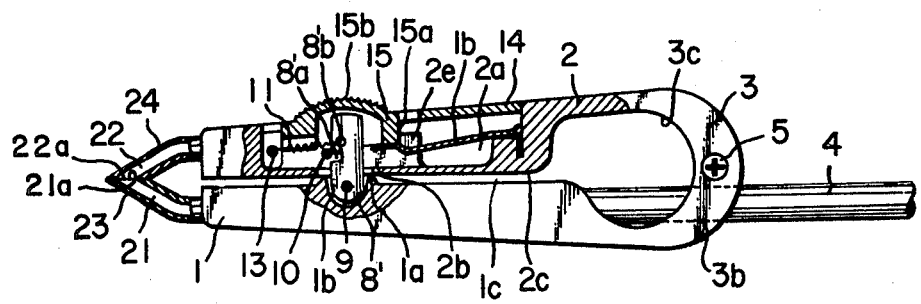
FIG. 3 shows another embodiment of the invention wherein the hair clamping members differ in shape from those of the embodiment shown in FIG. 2.
Figure 3A:
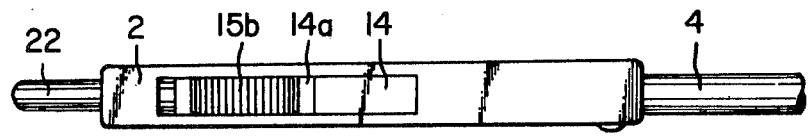
FIG. 3a is a plan view of the hair tweezer device shown in FIG. 3.
Figure 3B:
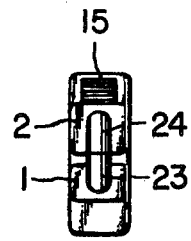
FIG. 3b is a side view of the hair tweezer device shown in FIG. 3.

FIGS. 3, 3a and 3b show another embodiment which differs from the embodiment shown in FIG. 2 in the shape of the hair clamping members. In the embodiment shown, the hair clamping members designated 21 and 22 are provided with heat insulating covers 23 and 24 respectively at the outer surfaces thereof. The high frequency wave conductor 4 which may be in the form of a sealed wire is connected to the hair clamping members 21 and 22 in the interior of the leg 1. The provision of the heat insulating covers 23 and 24 is effective to bring tips 21a and 22a of the hair clamping members 21 and 22 respectively into intimate contact with the human skin without causing injury thereto. This eliminates the need to use the safety guide 12 shown in FIG. 2. Because of the absence of the safety guide 12, the setting link 8' is not formed therein with the slit 8c for engaging one end of the safety guide 12. The abutting surfaces of the hair clamping members 21 and 22 are bare and not provided with the covers 23 and 24. The setting lever 15 of the embodiment shown in FIG. 3 is similar in construction to that of the embodiment shown in FIG. 2.

Figure 4:
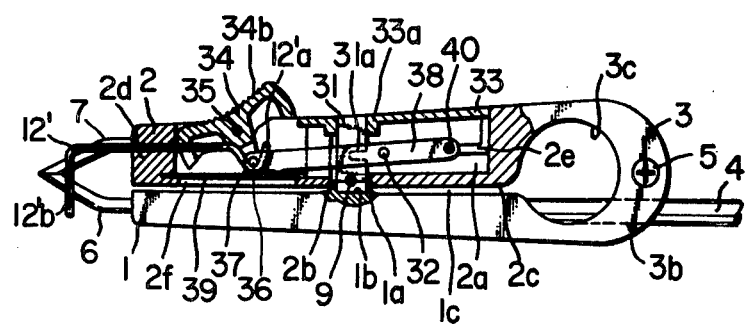
FIG. 4 is a front view, partly shown in section, of still another embodiment of the invention wherein the hair clamping members are of the same shape as those of the embodiment shown in FIG. 2 but the setting mechanism differs from that of the embodiment shown in FIG. 2.
Figure 4A:
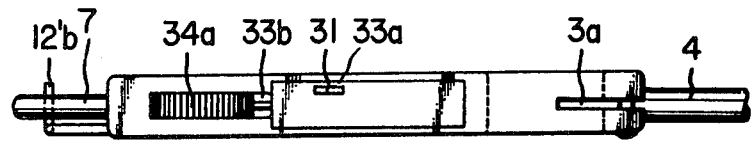
FIG. 4a is a plan view of the hair tweezer device shown in FIG. 4.
Figure 4B:
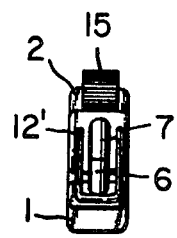
FIG. 4b is a side view of the hair tweezer device shown in FIG. 4.

FIGS. 4, 4a and 4b show en embodiment in which the hair clamping members are similar in shape to those of the embodiment shown in FIG. 2. However, the link mechanism arranged in the hollow space 2a of the leg 2 for moving the hair clamping members between their open and closed positions is distinct from the link mechanism of the embodiment shown in FIG. 2.

More specifically, a setting link 31 is supported by the pin 9 for pivotal movement relative to the support portion 1a of the leg 1. The setting link 31 is formed substantially in the middle of its lengthwise axis with a notch 31a for receiving therein a locking pin 32. A cover 33 for the hollow space 2a of the leg 2 is secured to the outer surface of the leg 2 and formed therein with a longitudinally disposed slit 33a for guiding the setting link 31, and with an opening 33b for inserting therein a setting lever 34 in the form of a setting lever for actuating and de-actuating the hair clamping members 6 and 7.

The setting lever 34 in the form of a toggle lever is formed on its outer periphery with a knurled surface 34a and pivotally supported substantially in its center by a pin 35 which is rotatably supported by opposite side walls of the leg 2 defining the hollow space 2a. The setting lever 34 is connected at its lower end to one end of a stopper link 38 through a pin 40 and a roller 37 which are loosely connected to the stopper link 38. The roller 37 presses against a plate spring 39 yieldably mounted in the hollow space 2a of the leg 2 so as to cause the setting lever 34 to perform a tumbling action, when the setting lever 34 is caused to move in pivotal motion. The stopper link 38 is slidably supported at the other end thereof through a pin 40 in a longitudinal guide groove 2e which is attached to the rear wall of the leg 2. Safety guide 12' is formed the same as the safety guide 12 in FIG. 2, and is joined to the setting lever 34 at pin 36.

Figure 5:
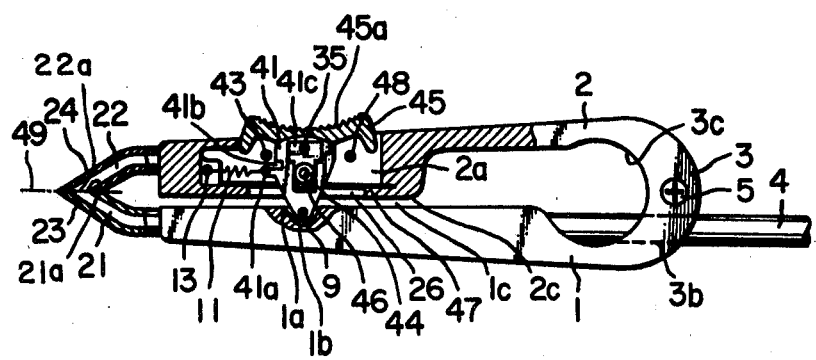
FIG. 5 is a front view, partly shown in section, of a further embodiment of the invention wherein the hair clamping members are of the same shape as those of the embodiment shown in FIG. 3 but the link mechanism differs from that of the embodiment shown in FIG. 3.
Figure 5A:
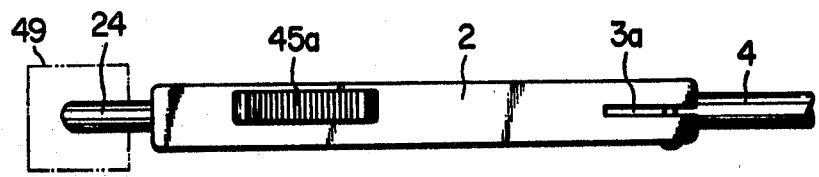
FIG. 5a is a plan view of the hair tweezer device shown in FIG. 5.
Figure 5B:
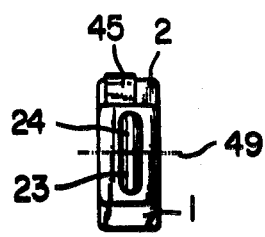
FIG. 5b is a side view of the hair tweezer device shown in FIG. 5.

FIGS. 5, 5a and 5b show an embodiment in which the hair clamping members are provided with heat insulating covers and the link mechanism for moving the hair clamping members between their open and closed positions is similar to the link mechanism of the embodiment shown in FIG. 4. A setting link 41 is fixed to the pin 9 rotatably supported by the support portion 1s of the leg 1, so that the setting link 41 can move in pivotal motion. The setting link 41 is formed therein with a notch 41b for receiving a locking pin 43, with a hole 41a for connecting one end of a spring 42 and with a T-shaped hollow space 41c for receiving a lever clamp roller 44. A setting lever 45 is supported by a pin 46 extending through the T-shaped opening 41c and supported at opposite ends thereof by the side walls of the leg 2 defining the hollow space 2a. The setting lever 45 has a roller 46 rotatably supported by a pin 46 attached to a lower end of the setting lever 45. Maintained is contact with and disposed beneath the roller 46 is a plate spring 47 which is connected at opposite ends thereof to front and rear walls of the leg 2. When setting lever 45 is caused to move in pivotal motion, the plate spring 47 is pressed by the roller 44 and slightly bent by the applied pressure so as to thereby cause the setting lever 45 to perform a tumbling action. The spring 11 is connected at the other end to the first wall of the leg 2. A rocking pin 43 and a stopper 48 for the setting link 41 extend across the hollow space 2a and are supported at opposite ends thereof by the side walls of the leg 2.

A heat dissipating plate 49 may be inserted between the tips 21a and 22a of the hair clamping members 21 and 22 respectively.

Figure 2A:
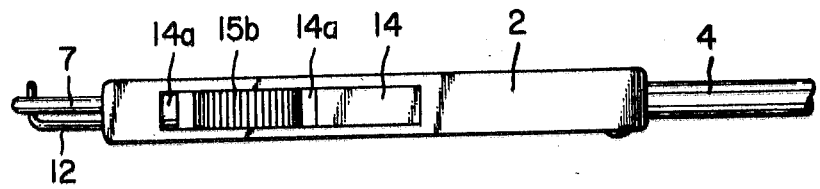
FIG. 2a is a plan view of the hair tweezer device shown in FIG. 2.
Figure 2B:
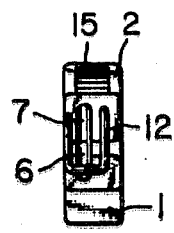
FIG. 2b is a side view of the hair tweezer device shown in FIG. 2.

The operation of the hair tweezer device in accordance with the present invention will now be described. In the embodiment shown in FIGS. 2, 2a and 2b, the high frequency wave conductor 4 is connected to a high frequency wave generator, not shown. When the hair tweezer device in accordance with the invention is put to use, the locking pin 10 is disengaged from the notch 8a formed in the setting link 8, so that the space between the legs 1 and 2 is increased and a small gap is formed between the tips 6a and 7a of the hair clamping members 6 and 7. Then pressure is applied by the finger to the knurled surface 15b of the setting lever 15 to move the same leftwardly in FIG. 2. The result of this is that the surface 15a of the setting lever 15 pushes and moves the setting link 8 leftwardly in FIG. 2, so that the setting link 8 moves in pivotal movement about the pin 9. This causes the safety guide 12, which is engaged in the slit 8c at the portion 12a, to move forward, so that the U-shaped forward end portion 12b is brought into contact with the skin. Thus the tips 6a and 7a of the hair clamping members 6 and 7 respectively are spaced apart from the skin a distance of over 1 millimeter. While the tips of the hair clamping members are spaced apart from the skin by the safety guide 12, the device is bodily moved to a position in which the tips 6a and 7a of the hair clamping members 6 and 7 are positioned against opposite sides of a hair. Then the setting lever 15 is further moved leftwardly as in FIG. 2. This causes the locking pin 10 to be engaged in the notch 8a formed in the setting link 8, so that the legs 1 and 2 are locked in position and the tips 6a and 7b of the hair clamping members 6 and 7 clamp the hair. After a lapse of a predetermined time interval, the hair clamped by the hair clamping members 6 and 7 is removed from the skin together with its root by the action of the high frequency waves. When the hair is thus plucked out, the setting lever 15 is moved rightwardly in FIG. 2 and the legs 1 and 2 are moved apart a greater distance from each other. The aforementioned cycle of operation is repeated for each hair to be plucked out.

In the embodiment of the invention shown in FIGS. 3, 3a and 3b, the hair clamping members 21 and 22 are provided with heat insulating covers 23 and 24 respectively. By this arrangement, the tips 21a and 22a of the hair clamping members 21 and 22 respectively are kept from coming into direct contact with the skin, so that the safety of the skin is assured at all times. Thus, the setting lever 15 only performs the function of moving the hair clamping members 21 and 22 between a position in which the tips thereof are in engagement with each other and a position in which the tips thereof are out of engagement with each other.

The embodiment of the invention shown in FIGS. 4, 4a and 4b operates as follows. In putting the hair tweezer device to use, the hair clamping members 6 and 7 are brought to a position in which their tips are disposed on opposite sides of a hair to be plucked out and spaced apart a small distance from the skin. The front end portion of the safety guide 12 must be brought into contact with the skin as is the case with the embodiment shown in FIG. 2 so as to prevent direct contact of the tips 6a and 7b of the hair clamping members 6 and 7 with the skin. To this end, the setting lever 34 in the form of a toggle lever is moved clockwise in FIG. 4. The movement of the setting lever 34 in the clockwise direction actuates the link mechanism and moves the safety guide 12' leftwardly in FIG. 4, so that the forward end portion 12b elongated forward of the joint 12'a is brought into contact with the skin. Further movement of the setting lever 34 in the clockwise direction brings the pin 32 attached to the setting lever 38 into engagement in the notch 31a formed in the setting link 31. This brings the legs 1 and 2 toward each other and hence the hair clamping members 6 and 7 into contact with each other, so that the hair is clamped by the tips 6a and 7a of the hair clamping members 6 and 7. After a lapse of a predetermined time interval, the hair clamped by the hair clamping members 6 and 7 is removed from the skin together with its root by the action of the high frequency waves. When the hair is thus plucked out, the setting lever 34 is moved in a counter-clockwise direction to release the pin 32 from the notch 31a formed in the setting link 31. Thus the legs 1 and 2 are moved apart a greater distance from each other and the tips 6a and 7a of the hair clamping members 6 and 7 are brought out of engagement with each other. The aforementioned cycle of operation is repeated for each hair to be plucked out.

The embodiment of the invention shown in FIGS. 5, 5a and 5b operates as follows. If the setting lever 45 is moved in a clockwise direction in FIG. 5, then the lever clamp roller 44 received in the T-shaped hollow space 41c formed in the setting link 41 moves within the T-shaped hollow space 41c. The result of this is that the roller 44 moves upwardly to an upper portion of the T-shaped hollow space 41c which has a greater width than its lower portion, so that the locking pin 43 is engaged in the notch 41b formed in the setting link 41. Thus the spacing between the legs 1 and 2 is reduced and the tips of the hair clamping members 21 and 22 are brought into engagement with each other to thereby clamp the hair. The roller 44 performs the function of causing the setting lever 45 to move in a tumbling motion when the roller presses against the plate spring 47. After a lapse of a predetermined time interval, the hair clamped by the hair clamping member 21 and 22 is removed from the skin together with its root by the action of the high frequency waves. Thereafter the setting lever 45 is moved in a counter-clockwise direction, thereby bringing the locking pin 43 out of engagement in the notch 41b formed in the setting link 41. The aforementioned cycle of operation is repeated for each hair to be plucked out.

From the foregoing description, it will be appreciated that the hair tweezer device provided by the present invention offers the advantage of preventing inadvertent contact of the hair clamping members with the skin by the safety device incorporated in the device, thereby ensuring that hairs can be plucked out with safety by application of high frequency waves.

What is claimed is:

1. A hair tweezer device for removing a hair growing implanted in skin in response to a high frequency wave provided to said hair, said tweezer comprising a main body substantially in the form of a letter U defined by a pair of elongated legs joined by a curved portion at a rearward end thereof, said curved portion being flexible; a conductor for said high frequency wave introduced through one of said legs; a hair clamping member extending axially forward from the open end of said U at a forward end of each one of said pair of legs, said hair clamping members being disposable in a spaced juxtaposed relationship and including a pair of confrontable tip surfaces capable of being brought into and out of confronting engagement with each other, said hair clamping members including said tip surfaces and being electrically connected to said high frequency wave conductor for providing said high frequency wave provided therethrough to said tip surfaces for providing heat therefrom to said hair; each of said pair of hair clamping members further comprising a heat insulating cover for providing a completely enclosed thermally conductive path to said tip surfaces insulated from the ambient environment for avoiding direct thermal contact of said hair clamping members with said skin when hair is clamped and said tips are in said confronting engagement; a setting lever mounted in one of said legs and movable between a first set position and a second set position and being partially exposed to the outside; and a link mechanism operatively connected to said setting lever and mounted in said two legs, said link mechanism including a setting link operatively connected to said setting lever for moving said setting link in a pivotal motion for bringing said tip surfaces into said confronting engagement with each other when said setting lever is set in said first position and out of said engagement with each other when said setting lever is set in said second position, said tip surfaces being movable into and out of said engagement by utilizing the flexibility of said curved portion for enabling said hair to be releasably clamped when said setting lever is set in said first position while said high frequency wave is provided to said tip surfaces and therethrough to said clamped hair; whereby said hair clamping members can clamp said hair, transmit heat thereto through said tip surfaces in response to said high frequency wave and pluck out said clamped hair from said skin in one operation while avoiding said direct thermal contact of said hair clamping members with said skin.

* * * * *